United States Patent [19]

Shmidel et al.

[11] 4,221,668
[45] Sep. 9, 1980

[54] METHOD, APPARATUS AND SYSTEM FOR PRODUCING ELUENT FLOW IN LIQUID CHROMATOGRAPHY

[76] Inventors: Evgeny B. Shmidel, ulitsa Profsojuznaya, 97, korpus 1, kv. 139; Viktor G. Berezkin, Leninsky prospekt, 40, kv. 54; Ljudmila N. Kolomiets, ulitsa Avangardnaya, 12, kv. 60; Julia L. Sheftelevich, ulitsa Profsojuznaya, 97, korpus 1, kv. 139; Valery E. Shepelev, ulitsa Khalturninskaya, 4, korpus 2, kv. 28, all of Moscow, U.S.S.R.

[21] Appl. No.: 36,174

[22] Filed: May 4, 1979

[30] Foreign Application Priority Data

May 5, 1978 [SU] U.S.S.R. ................. 2606052
May 5, 1978 [SU] U.S.S.R. ................. 2606053

[51] Int. Cl.² .............................. B01D 15/08
[52] U.S. Cl. ..................... 210/635; 210/198 C; 210/321 R
[58] Field of Search ............. 210/31 C, 198 C, 321 A

[56] References Cited

U.S. PATENT DOCUMENTS

| 3,984,315 | 10/1976 | Ernst et al. | 210/198 C |
| 4,043,906 | 8/1977 | Helmer | 210/198 C |
| 4,124,488 | 11/1978 | Wilson | 210/321 R |

OTHER PUBLICATIONS

Introduction to Modern Liquid Chromatography by Snyder et al., John Wiley & Sons, New York, N.Y., 1974, Chapter 4.

Primary Examiner—John Adee
Attorney, Agent, or Firm—Burgess, Ryan and Wayne

[57] ABSTRACT

A method for producing a flow of an eluent in liquid chromatography according to the present invention comprises displacing the eluent into a chromatographic column under the effect of an osmotic pressure of a solution of a substance with its concentration being maintained constant. An apparatus for performing said method comprises a source of pressure and a container with the eluent communicating with said source of pressure; the latter comprising an osmotic system consisting of two vessels and a semi-permeable membrane partitioning said vessels; one of the vessels is filled with a solvent, while the other is communicating with the container and filled with a saturated solution of the substance contacting with the substance in the solid phase disposed in the same vessel. A system for producing a flow of an eluent in liquid chromatography according to the present invention consists of at least two said apparatus series-connected therebetween.

The method for producing an eluent flow in liquid chromatography according to the present invention makes it possible to obtain a uniform flow of an eluent without pulsations within a wide range of pressures employed in liquid chromatography.

The apparatus for performing the method of the invention has no moving parts and eliminates contamination of the eluent.

9 Claims, 5 Drawing Figures

METHOD, APPARATUS AND SYSTEM FOR PRODUCING ELUENT FLOW IN LIQUID CHROMATOGRAPHY

FIELD OF THE INVENTION

The present invention relates to liquid chromatography and, more specifically, to methods for producing an eluent flow in liquid chromatography, apparatus and systems for producing an eluent flow in liquid chromatography based on said apparatus.

BACKGROUND OF THE INVENTION

Currently known in the art are several methods for producing an eluent flow in liquid chromatography. A uniform eluent flow in liquid chromatography is an obligatory precondition for carrying-out a chromatographic analysis.

One of methods of producing an eluent flow in liquid chromatography comprises displacement of the eluent through a chromatographic system under pressure.

As the source of pressure use is made of pumps of different designs (cf. Modern Practice of Liquid Chromatography Edited by J.J. Kirkland. Industrial and Biochemical Department E.I. du Pont de Nemours and Company, Wilmington, Delaware, Wiley Interscience, a Division of John Wiley and Sons, Inc., New York, London, Sydney, Toronto, 1971, Chap. 2)

This prior art method has certain disadvantages among which most important are occurence of pulsations and a high cost of the equipment required for carrying it out. Furthermore, in modern liquid chromatography a wide range of pressures is employed to ensure a required rate of flowing of the eluent through a chromatographic column. Variation of the flow rate of the eluent is associated with a delicate and labour-consuming operation of the pump adjustment for a different pressure thus prolonging the analysis duration and hindering the shift from one flow rate of the eluent to another.

Known in the art is a method for producing a uniform flow of an eluent in liquid chromatography by way of displacing the eluent from a container under pressure of a compressed gas which is supplied to a resilient partition or a piston mounted in said container with the eluent.

This prior art method is realized by means of an apparatus for producing an eluent flow in liquid chromatography, e.g. by means of a pneumatic pump comprising a rigid container with a located therein compressible vessel with an eluent. In this pump, a compressed gas is fed into the rigid container thus compressing the vessel and displacing the eluent out of it. In different arrangements of the pump as the compressible vessel use is made of a plastic flask, stainless-steel or teflon bellows (cf. Modern Practice of Liquid Chromatography, Edited by J.J. Kirkland, Industrial and Biochemical Department, E.I. du Pont de Nemours and Company, Wilmington, Delaware, Wiley Interscience, a Division of John Wiley and Sons, New York, London, Sydney, Toronto, 1971, Chap. 2).

However, the above-described prior art method and corresponding apparatus for producing a flow of an eluent in liquid chromatography feature a series of essential disadvantages.

Due to the evolution of the dissolved gases from the eluent, chromatographic parameters are impaired, for example resolution, and stability of operation of the sensor of zero-line fluctuations is hindered.

To practice said prior art method using the above-described apparatus a high-pressure source is required, i.e. a container with a compressed gas. As a result, the whole chromatographic system becomes cumbersome and inconvenient in transportation and lacks its self-dependency.

Said cylinders with compressed gas operate under pressure not exceeding 150 atm, whereby the upper pressure limit of this pump system becomes restricted.

SUMMARY OF THE INVENTION

It is an object of the present invention to provide such a method for producing a flow of an eluent in liquid chromatography, such an apparatus therefor and such a system based on said apparatus which would make it possible to create a uniform eluent flow without pulsations under any pressure employed in liquid chromatography.

This object is accomplished by a method for producing an eluent flow in liquid chromatography by way of displacing the eluent into a chromatographic column under pressure, wherein in accordance with the present invention the displacement of the eleunt is ensured by the effect of osmotic pressure of a solution of a substance, the solution concentration being maintained constant.

In the case where as the eluent use is made of the same substance solution as for the creation of osmotic pressure, the method for producing an eluent flow in liquid chromatography is substantially simplified.

The constant concentration of the substance solution should be preferably maintained by contacting same with this substance in the solid phase thereof, the substance solution being thermostatted at a temperature above the freezing point of the solvent.

An apparatus intended for carrying-out the method according to the present invention comprises a source of pressure and a container with the eluent communicating with this source; in accordance with the present invention, the pressure source comprises an osmotic system embodied in the form of two vessels and a semi-permeable membrane separating said vessels, one of which vessels being filled with the container and filled with a saturated solution of the substance contacting with the solid-phase substance contained in the same vessel.

To ensure mechanical strength of the semi-permeable membrane, a sunstrate is provided in the osmotic system; on the surface of said substrate, from the side thereof opposite to the solvent stream, said semi-permeable membrane is disposed.

In the case where it is required to increase the working pressure, it is advisable to use a system for producing a flow of an eluent in liquid chromatography composed of at least two series connected similar apparatus for producing an eluent flow in liquid chromatography.

The present invention is embodied in the following manner.

In one of said vessels a solvent is poured which, through the semi-permeable membrane is contacted with the solution of a substance contained in the other vessel. In turn, the vessel with the substance solution is communicated with the container, wherein the eluent is place. In the case where as the eluent use is made of the same substance solution, a chromatographic column can be directly attached to the vessel with the substance solution.

The displacement of the eluent into the chromatographic column is effected under the osmotic pressure of the substance solution, the concentration of the latter being maintained constant. The osmotic pressure begins to create at the moment when the vessel with the substance solution is brought into contact with the solvent. The solvent starts to penetrate through the semi-permeable membrane thus increasing the total volume of the substance solution thus resulting in the displacement of the eluent under a specific pressure at a constant flow rate. At the present time for concentrated solutions there have not been sufficiently studied the parameters defining the value of the osmotic pressure, as well as the functional relationship between said parameters. Evaluation of osmotic pressures of diluted solutions may be effected following the Vanit-Hoff equation. The concentration of the substance is maintained constant, for example, by contacting it with the same substance in the solid phase. To provide a constant temperature of the solution, the vessel with the substance solution is thermostatted.

Increased flow rate of the eluent and increased pressure value can be obtained by selecting corresponding pairs of the substance and solvent, type and surface of membranes, thermostatting temperature.

In the method according to the present invention use may be made of solutions of various compounds. As the substance use may be made of both organic and inorganic compounds such as $LiCl$, $NaCl$, $NH_4Cl$, $CaCl_2$, $BaCl_2$, $MgCl_2$, $KCl$, $MgClO_4$, $LiNO_3$, $Ca(NO_3)_2$, $Mg(NO_3)_2$, $NaNO_3$, $Na_2SO_4$, $MgSO_4$, $CuSO_4$, $MnSO_4$, $AlCl_3$, $NaOH$, $KH_2PO_4$, $(CH_3COO)_2Mg$, cellulose nitrate, sugars, hemoglobin, gelatine, and mixtures of compounds such as CsCl-KCl, sea salt, salt-lake salts. It is most convenient to employ aqueous solutions of substances, though it is possible to use other solvents.

The present invention is further illustrated by the description of particular embodiments thereof with reference to the accompanying drawings, wherein.

Figure 1:
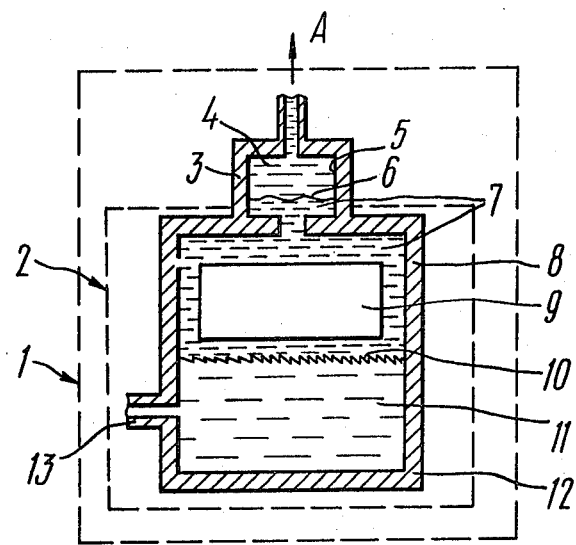
FIG. 1 is a schematic elevation view of longitudinal a section of an embodiment of the apparatus according to the present invention intended for performing the method of the present invention.

The apparatus 1 (FIG. 1) for producing an eluent flow in liquid chromatography contains a pressure source 2 in the form of an osmotic system and communicating therewith a container 3 with an eluent 4.

The eluent is in a vessel 5 of the rigid container 3; the vessel volume is limited by means of a movable impermeable partition 6. The volume of said vessel 5 may be also limited by the interface between the eluent and a saturated solution of a substance 7 immiscible therewith and disposed in a vessel 8 of the osmotic system 2 communicating with the rigid container 3. In the vessel 8, apart from said saturated solution 7, there is the substance in the solid phase 9; said saturated solution and the solid-phase substance being separated by a semi-permeable membrane 10 from a solvent 11. The solvent 11 is in a vessel 12 of the osmotic system 2 provided with an inlet pipe 13 for the supply of the solvent 11. With the use of the apparatus according to this embodiment of the present invention, for the provision of great pressures and a high mechanical strength of the semi-permeable membrane 10 (FIG. 1), the latter is positioned on a substrate 14 (FIG. 2).

As semi-permeable membranes use may be made of porous: dynamic, pre-moulded, sealing, rigid-structure, composite, isotropic, anisotropic, deposited, impregnated, sprayed-on, and applied membranes. Also used may be non-porous: (diffusional), sealing, rigid-structure, isotropic, anisotropic membranes.

Figure 2:
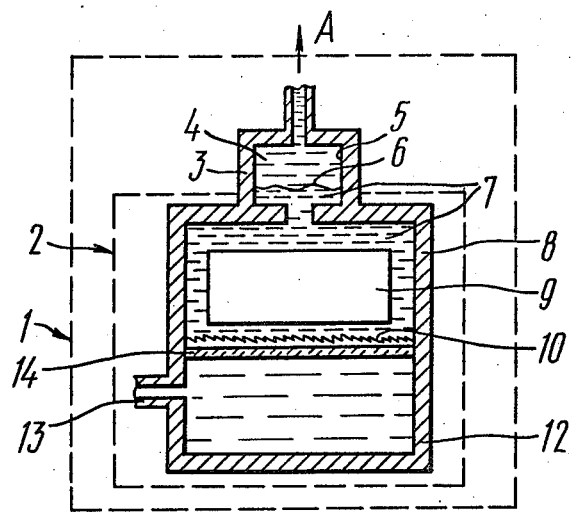
FIG. 2 is an elevation view of a longitudinal section of another embodiment of the apparatus for performing the method according to the present invention.

In the case of the necessity to increase the working pressure, the present invention provides for a system for producing an eluent flow in liquid chromatography consisting of at least two series-connected similar apparatus 1 as shown in FIG. 2. This system is shown in FIG. 3; for the purpose of convenience of the description of operation of said system, structure members of one of the apparatus have reference characters different from those for similar members of the other apparatus.

Figure 3:
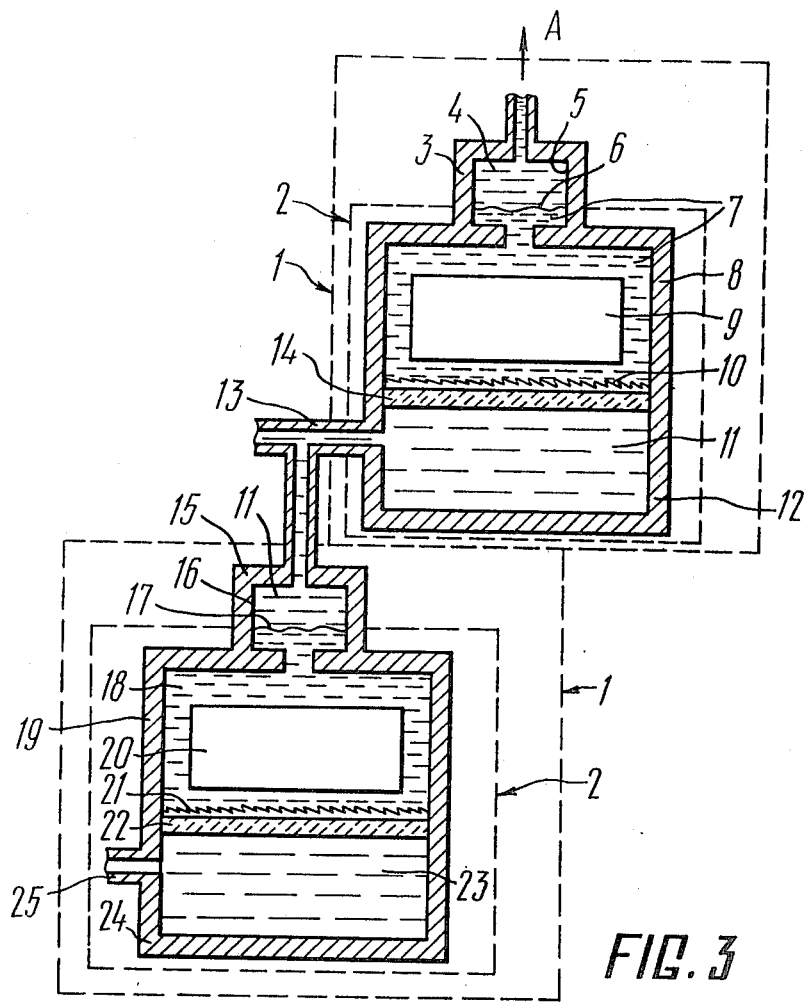
FIG. 3 is an elevation view of a longitudinal section of a system incorporating two similar apparatus of FIG. 2 series connected therebetween and intended to perform the method according to the present invention.

The system for producing an eluent flow in liquid chromagography comprises an apparatus 1 (FIG. 2) which communicates, through an inlet pipe 13 (FIG. 2) for the supply of a solvent, to the outlet of the rigid container 15 (FIG. 3) of the second similar apparatus 1 (FIG. 3).

The second similar apparatus is a rigid container 15 containing a solvent 11 in a resilient vessel 16 (the same solvent which is present in the vessel 12, FIG. 1). The solvent 11 is separated by means of a movable partition 17 from a saturated solution of a substance 18 stored in a container 15 communicating with a vessel 19 of the osmotic system 2, wherein there are a saturated solution of the substance 18 and the same substance in the solid phase 20 separated by means of a semi-permeable membrane 21 on a substrate 22 from the solvent 23 contained in another vessel 24 of the osmotic system 2 which is also provided with the inlet pipe 25 for the supply of the solvent.

The operation of the apparatus for performing the method for producing an eluent flow in liquid chromatography is illustrated in FIG. 1. At the initial stage, into the resilient vessel 5 of the container 3 the eluent 4 is poured and the outlet of the container 3 is connected to a chromatographic column. Into the vessel 12 the same solvent 11 (which is used for dissolution of the substance 7) is fed through the pipe 13. Then into the vessel 8 there is poured a saturated solution of the substance 7 and the same substance in the solid phase 9 is added in such an amount (Q) which ensures a constant concentration ($C_s$) of the saturated solution of the substance in the vessel 8 within the predetermined time period ($\tau$) at the selected flow rate of the eluent ($\alpha$). The amount of the solid substance is determined according to the following relationship:

$$Q = K \cdot C_s \cdot \alpha \cdot \tau,$$

wherein K is a proportionality factor.

Upon contacting the solvent 11 with the semi-permeable membrane 10, an osmotic pressure starts to increase in the vessel 8 due to the penetration of the solvent 11 into the substance solution 7; under this osmotic pressure the saturated substance solution 7 is displaced from the vessel 8 to the container 3 with the eluent 4. Under the effect of the osmotic pressure of the saturated solution of the substance 7 the resilient impermeable partition 6 or the interface between the eluent and immiscible therewith saturated solution of the substance 7 starts to move thus resulting in the displacement of the eluent 4 from the container 3 to the chromatographic column (the direction of movement of the displaced eluent towards the chromatographic column is shown by arrow A).

To increase the working pressure, apart from the selection of appropriate pairs solvent-solution, use may be made of the system for producing an eluent flow in liquid chromatography as presented in FIG. 3.

Operation of this system is effected in the following manner.

At the initial stage, into the resilient vessel 5 (FIG. 3) of the container 3 the eluent 4 is poured and the outlet of the container 3 is connected to the chromatographic column. Into the vessel 12 through the inlet pipe 13 the same solvent (as the solvent 11 which is poured to fill the resilient vessel of the container 15) is admitted; the outlet of the container 15 is connected to the pipe 13. Into the vessel 24 through the inlet pipe 25 the solvent 23 is poured which may be the same as the solvent 11 or different. Into the vessels 8 and 19 the substance in the solid phase 9 and 20 is introduced (this substance may be the same or different). Said vessels are filled with saturated solutions of corresponding substances 7 and 18. Upon contacting of the solvent 23 through the semi-permeable membrane 21 on the substrate 22 with the solution of the substance 18 the solvent 23 starts to penetrate into the vessel 19, wherein an osmotic pressure begins to increase. Under the effect of this pressure the saturated solution of the substance 18 displaces the solvent 23 from the resilient vessel 16 of the container 15 to the vessel 12 communicating with the container 15 through the pipe 13 thus increasing the initial pressure of the solvent 11 of the subsequent osmotic system. The solvent 11, in turn, penetrates through the semi-permeable membrane 10 into the vessel 8 with the dissolved substance 7 and creates an osmotic pressure therein which is equal to the total of the values of the osmotic pressures created in the two osmotic systems.

Under this pressure the eluent 4 is displaced to the chromatographic column from the resilient vessel 5 of the container 3.

The present invention makes it possible to produce a uniform flow of an eluent in liquid chromatography without pulsation within a wide range of pressures employed in liquid chromatography.

Furthermore, the method according to the present invention is very simple as to the equipment employed. In the apparatus intended to perform the method according to the present invention there are no moving parts. The method according to the present invention eliminates contamination of the eluent with impurities, unlike this occurs in the prior art systems due to the operation of pump systems.

For a better understanding of the present invention some specific Examples are given hereinbelow by way of illustration.

EXAMPLE 1

Into a steel vessel 12 with the internal volume of 200 ml a solvent, i.e. water, is admitted through the inlet pipe 13. The resilient vessel 5 with the capacity of 500 ml is filled with heptane. A solid salt of $MgSO_4$ in the amount of 200 g sufficient to displace the total volume of the eluent is placed into the vessel 8 with the inner volume of 500 ml. Then into the vessel 8 a saturated aqueous solution of $MgSO_4$ is poured. The vessel 12 is separated from the vessel 8 by means of a semi-permeable membrane 10 made of a cellulose-acetate film supported by a cermet substrate 14. The surface area of the membrane is equal to 25 $cm^2$.

Water, from the side of the cermet substrate, penetrates into the vessel 8 thus creating an osmotic pressure thereinside. The pressure at the inlet of the chromatographic column and the eluent flow rate therethrough are maintained constant until the solid salt $MgSO_4$ is completely dissolved in water supplied into the vessel 8. At the constant flow rate of heptane of 4 ml/hr the pressure at the column inlet is 120 atm.abs.

EXAMPLE 2

The procedure of the foregoing Example 1 is repeated, except that as the semi-permeable partition use is made of a plasma-deposited 4-vinylpyridine membrane supported on the "Millipore" substrate produced by the "Millipore" Inc. The eluent flow rate is 60 ml/hr under the pressure of 78 atm.abs.

EXAMPLE 3

The procedure of the foregoing Example 1 is repeated, except that the resistance of the chromatographic column is varied by decreasing its length. At the constant flow rate of heptane of 12 ml/hr the pressure at the column inlet is equal to 40 atm.abs.

EXAMPLE 4

The procedure of Example 1 hereinbefore is repeated, except that a saturated aqueous solution of saccharose is poured into the vessel 8.

At the constant flow rate of the eluent of 10 ml/hr the pressure at the inlet of the chromatographic column is equal to 110 atm.abs.

EXAMPLE 5

The procedure of the foregoing Example 1 is repeated, except that into the vessel 8 threre is poured a saturated solution of cellulose nitrate in cyclohexanone, while cyclohexanone is poured into the vessel 12 and as the membrane use is made of a polyimide film.

At the constant flow rate of the eluent of 6 ml/hr the pressure at the inlet of the chromatographic column is 90 atm.abs.

EXAMPLE 6

The procedure of Example 1 hereinbefore is repeated, except that into the vessel 8 there is poured a saturated solution of saccharose in ethanol, while into the vessel 12 ethanol is poured.

At the constant flow rate of the eluent of 9 ml/hr the pressure at the inlet of the chromatographic column is 70 atm.abs.

EXAMPLE 7

The process is performed in a manner similar to that described in Example 1 hereinbefore, except that into the vessel 8 there is poured an saturated solution of cellulose nitrate in ethylacetate, while into the vessel 12 ethylacetate is poured; as the membrane material use is made of an acrylonitrile film.

At the constant flow rate of the eluent of 6 ml/hr the pressure at the inlet of the chromatographic column is equal to 64 atm.abs.

EXAMPLE 8

The system for the production of a flow of an eluent in liquid chromatography as shown in FIG. 3 of the accompanying drawings consists of two apparatus described in Example 1 hereinbefore and similar as to their dimensions and structure materials.

At the initial stage into the resilient vessel 5 (FIG. 3) of the container 3 there is poured heptane 4 and the outlet of the container 3 is connected with a chromatographic column. Water is admitted into the vessel 12 through the inlet pipe 13. The flexible vessel 16 of the container 15 is also filled with water, while the outlet of the container 15 is connected to the pipe 13. A solvent, i.e. water, is admitted into the vessel 23 through the inlet pipe 25. A solid salt $MgSO_4$ (9, 20) is introduced into the vessels 8 and 19 in the abount of 200 g per each vessel. Thereafter, into the same vessels 8 and 19 there are poured saturated aqueous solutions of $MgSO_4$ (7 and 18).

Upon the contact between water and the saturated $MgSO_4$ solution 18 through the semi-permeable membrane 21 water starts to penetrate into the vessel 19, wherein an osmotic pressure starts to develop. Under the effect of this pressure the saturated aqueous solution 18 of $MgSO_4$ displaces water from the resilient vessel 16 of the container 15 into the vessel 12 connected with the container 15 by means of the pipe 13, thus increasing the initial pressure of water contained in the vessel 12. This water, in turn, due to the penetration through the semi-permeable membrane 10 made of a cellulose-acetate film disposed on a cermet substrate 14, passes into the vessel 8 containing a saturated aqueous solution of $MgSO_4$ and creates an osmotic pressure therein which is equal to the total of the values of osmotic systems. The osmotic pressure is equal to 235 atm.abs. Under this pressure, heptane 4 is displaced into the chromatographic column from the resilient vessel 5 of the container 3.

At a double length of the column as compared to the column length in the foregoing Example 1, the flow rate of heptane equal to 4 ml/hr is obtained under the pressure of 235 atm.abs.

EXAMPLE 9

Figure 4:
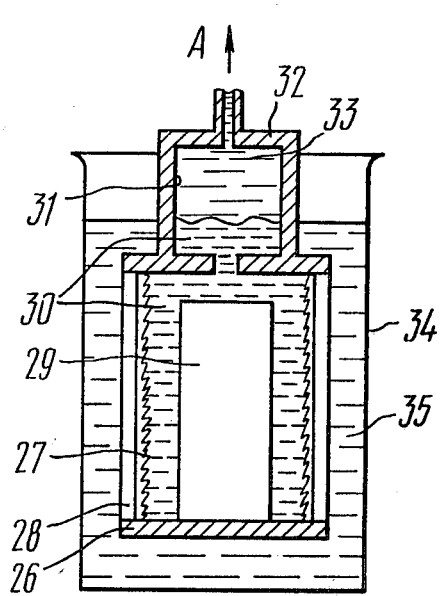
FIG. 4 is an elevation view of a longitudinal section an embodiment of an apparatus intended for performing the method according to the present invention.

Into a 1,000 ml steel vessel 26 (FIG. 4) with the cylindrical portion of its surface comprising a semi-permeable membrane 27 made of an aromatic polyamide film with the surface area of 180 $cm^2$ on a substrate 28 made of a reinforced cermet, a solid salt of $Ca(NO_3)_2$ (29) is preliminary charged in the amount of 450 g.

Into the same vessel 26 there is poured a saturated aqueous solution 30 of $Ca(NO_3)_2$. A 500 ml resilient vessel 31 of a rigid container 32 is filled with heptane 33 and connected to a chromatographic column. The filled vessel 26 is placed into a tank 34 containing a solvent 35, i.e. water. As soon as the vessel 26 is placed into the tank 34, water starts penetrating through the semi-permeable membrane 27 to the vessel 26 creating an osmotic pressure therein. Under the effect of this pressure heptane is displaced into the chromatographic column.

The range of the working pressure values created in this osmotic system is of from 5 to 150 atm.abs. Under the pressure of 150 atm.abs. the flow rate of heptane employed as the eluent is 18 ml/hr.

EXAMPLE 10

Into a 1,000 ml titanium vessel 26 (FIG. 4) with the cylindrical portion of its surface being also constituted by a semi-permeable partition 27 made of polyvinylchloride supported on a reinforced cermet substrate 28, a solid salt NaCl (29) is preliminary charged. Into the same vessel 26 a saturated aqueous solution 30 of NaCl is also charged. In contrast to Example 4 hereinbefore, in this Example the role of the eluent is taken by the saturated aqueous solution 30 of NaCl. The outlet of the vessel 26 is connected to the chromatographic column (not shown). The vessel 26 is placed into a tank 34 filled with a solvent 35 which is water. As soon as the vessel 26 is placed into the tank 34, water starts penetrating through the semi-permeable partition 27 to the vessel 26 thus creating an osmotic pressure therein; under this pressure the saturated aqueous solution 30 of NaCl is displaced into the chromatographic column. The predetermined flow rate of the saturated aqueous solution of NaCl equal to 60 ml/hr is obtained under the pressure of 48 atm.abs.

EXAMPLE 11

The procedure of the foregoing Example 9 is repeated, except that use is made of a saturated aqueous solution of $CH_3COONa$.

The given flow rate of the eluent equal to 60 ml/hr is ensured under the pressure of 57 atm.abs.

EXAMPLE 12

Figure 5:
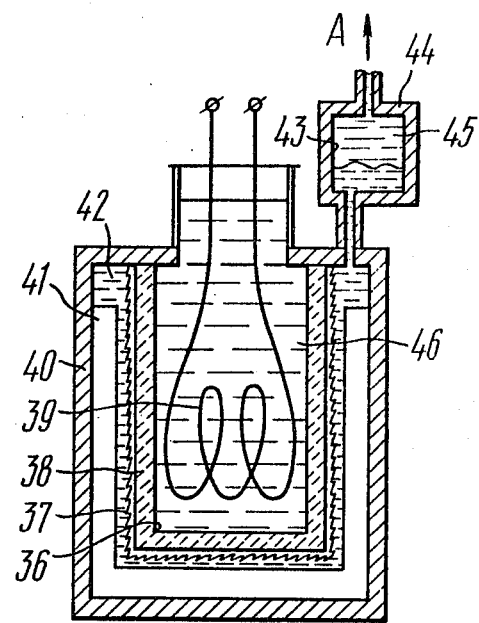
FIG. 5 is an elevation view of a longitudinal section of another embodiment of an apparatus for realization of the method according to the present invention.

A 120 ml vessel 36 (FIG. 5) with its walls comprising a semi-permeable membrane 37 made of polyvinylchloride supported on a reinforced cermet substrate 38 is provided with a heater 39. Into a 600 ml steel vessel 40 there are charged 250 g of $Mg(NO_3)_2$ (41) and its saturated aqueous solution 42 is also charged thereinto at the temperature of 25° C. Into a 500 ml resilient vessel 43 of a rigid container 44 hexane 45 is poured and the outlet of the container 44 is connected to a chromatographic column.

The vessel 40 is communicating with the container 44. Thereafter, into the vessel 36 a solvent 46, which is water, is charged and the solvent 46 is thermostatted at the temperature of 50° C. by means of the heater 39. As soon as water is poured into the vessel 36, it starts penetrating through the semi-permeable membrane 37 into the vessel 40, thus creating an osmotic pressure therein. Under said pressure hecane is displaced into the chromatographic column. Depending on the thermostatting temperature, the value of osmotic pressure is different and, hence, the flow rate of the eluent through the chromatographic column is varied. The predetermined flow rate of the saturated aqueous solution of $Mg(NO_3)_2$ equal to 30 ml/hr is ensured at the temperature of 50° C. under the osmotic pressure of 190 atm.abs.

What is claimed is:

1. A method for producing a flow of an eluent in liquid chromatography comprising displacing the eluent to a chromatographic column under the effect of osmotic pressure of a substance solution with its concentration being maintained constant.

2. A method as claimed in claim 1, wherein as the substance use is made of $Mg(NO_3)_2$, $MgSO_4$, NaCl, $Ca(NO_3)_2$, $CH_3COONa$, cellulose nitrate, cellulose, saccharose.

3. A method as claimed in claim 1, wherein as the solvent use is made of water, ethanol, ethylacetate, cyclohexanone.

4. A method as claimed in claim 1, wherein as the eluent use is made of the same substance solution as for the creation of °smotic pressure.

5. A method as claimed in claim 1, wherein the constant concentration of the substance solution is maintained by contacting thereof with the same substance in the solid phase, the substance solution being thermostatted at a temperature above the freezing point of the solvent.

6. An apparatus for producing a flow of an eluent in liquid chromatography comprising a container with an eluent and communicating therewith a pressure source comprising an osmotic system consisting of two vessels and a semi-permeable membrane partitioning said vessels, one of said vessels being filled with a solvent and the other vessel communicating with the container and filled with a saturated solution of the substance contacting with the substance in the solid phase disposed in the same vessel.

7. An apparatus as claimed in claim 6, wherein in said osmotic system a substrate being provided and said semi-permeable membrane being located on the surface of said substrate from the side thereof opposite to the solvent stream.

8. An apparatus as claimed in claim 6, containing as the semi-permeable membrane cellulose-acetate, polysulphonic, polyimide and acrylonitrile membranes.

9. A system for producing a flow of an eluent in liquid chromatography comprising at least two apparatus connected therebetween for producing a flow of an eluent in liquid chromatography, each of said apparatus having a container with an eluent and communicating with said container a source of pressure comprising an osmotic system consisting of two vessels and a semi-permeable membrane partitioning said vessels, one of said vessels being filled with a solvent, while the other vessel being communicated with said container and filled with a saturated solution of the substance contacting with the substance in the solid phase disposed in the same vessel.

* * * * *